United States Patent
Cewers

(10) Patent No.: US 6,289,891 B1
(45) Date of Patent: Sep. 18, 2001

(54) SAFETY SYSTEM AND METHOD FOR PREVENTING MIXING OF DIFFERENT ANAESTHETICS IN AN ANAESTHESIA SYSTEM

(75) Inventor: Göran Cewers, Lund (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 09/435,026

(22) Filed: Nov. 5, 1999

(30) Foreign Application Priority Data

Nov. 11, 1998 (SE) .................................................. 9803861

(51) Int. Cl.[7] .................................................. A61M 16/00
(52) U.S. Cl. .............................. 128/203.12; 128/205.23; 128/203.13; 128/204.22; 128/202.22
(58) Field of Search ........................ 128/203.12, 205.23, 128/203.13, 204.22, 910, 202.22

(56) References Cited

U.S. PATENT DOCUMENTS 3,910,222 * 10/1975 Metivier .................................. 116/70
4,934,358 * 6/1990 Nilsson et al. ..................... 128/200.23
5,293,865 * 3/1994 Altner et al. ...................... 128/203.12
5,537,992 * 7/1996 Bjoernstijerna et al. ......... 128/203.14
5,572,992 * 11/1996 Kankkunen et al. ............. 128/203.14
5,730,119 * 3/1998 Lekholm .......................... 128/200.24
5,824,885 * 10/1998 Lekholm ............................. 73/53.01
5,957,129 * 9/1999 Tham et al. ...................... 128/204.28

FOREIGN PATENT DOCUMENTS 0 727 654    8/1996 (EP) .

\* cited by examiner

Primary Examiner—John G. Weiss
Assistant Examiner—Mital Patel
(74) Attorney, Agent, or Firm—Schiff Hardin & Waite

(57) ABSTRACT

A safety system prevents inadvertent mixing of different anaesthetic agents, during replenishment wherein a new anaesthetic is replenished from a container to an anaesthesia machine containing a flow channel for the delivery of liquid anaesthetic, with a first anaesthetic being present downstream from the flow channel. Inadvertent mixing of different anaesthetics is avoided because the safety system has a measurement unit for identifying the new anaesthetic before the new anaesthetic comes into contact with the first anaesthetic. The measurement unit is arranged upstream from the first anaesthetic.

8 Claims, 2 Drawing Sheets

SAFETY SYSTEM AND METHOD FOR PREVENTING MIXING OF DIFFERENT ANAESTHETICS IN AN ANAESTHESIA SYSTEM

BACKGROUND OF THE INVENTION

1. Field of the Invention

The present invention is directed to a method and to an apparatus for preventing mixing of different anaesthetics in an anaesthesia system.

2. Description of the Prior Art

During anaesthesia, the patient is usually supplied with a gas mixture containing nitrous oxide, oxygen and an anaesthetic. Generally, one of the anaesthetics desflurane, enflurane, isoflurane, halothane or sevoflurane is the anaesthetic employed. These are all liquid at room temperature (even though desflurane has a boiling point very close to normal room temperature).

The anaesthetic administered to the patient therefore is vaporized in an anaesthesia machine connected to the patient. Vaporization is usually performed by a vaporizer that can be devised in many ways. A number of different kinds of vaporizers are described in the literature and are well known to those skilled in the art. Since details of the vaporizer design and function are not of essential relevance to the present invention, they need not be specified below.

Since some liquid anaesthetic is consumed, however, occasions arise when the anaesthesia machine needs to be replenished with new anaesthetic.

Erroneous replenishment with an anaesthetic other than the anaesthetic currently in the anaesthesia machine is always a possibility, thereby posing a major risk to the patient.

Since the patient is at great risk during anaesthesia, there are a number of known procedures available for avoiding mixing.

One known procedure involves indexing. This means that the cylinders containing anaesthetics have different features. One known procedure entails assigning each anaesthetic a unique color. The contents of a color-coded cylinder may only be added to a correspondingly color-coded vaporizer in the anaesthesia machine.

Since this procedure is obviously not foolproof, systems employing this technique can be augmented with mechanical indexing, i.e. a cylinder of anaesthetic will only mate with a vaporizer equipped with a corresponding receptacle.

Even though this combination is safer than color coding alone, it is not completely safe. This is because different vaporizers around the world do not fit this indexing system because of their age or use of alternative technology. Vaporizers are sometimes emptied after use and the evacuated anaesthetic is re-used for inducing subsequent anaesthesia.

Yet another known procedure is to arrange a measurement unit inside the anaesthesia machine, either in the anaesthesia machine's gas flow paths or in an anaesthetic vessel in a vaporizer. The measurement unit is able to identify the anaesthetic, and anaesthesia can be stopped and/or an alarm sounded if the system detects any mixture of anaesthetics in the gas flow paths.

Since anaesthetics have similar molecular structures, they also have very similar properties. Therefore, reliable identification of even "pure" anaesthetic is difficult. Identifying mixtures of anaesthetics is even more difficult.

SUMMARY OF THE INVENTION

An object of the present invention is to provide a safety system able to identify, more safely and effectively than hitherto, the situation in which inadvertent mixing of anaesthetics is imminent during replenishment with a new anaesthetic.

Another object of the present invention is to provide a safety system that safely and effectively prevents inadvertent mixing of anaesthetics in an anaesthesia machine.

Another object of the invention is to provide a method for avoiding inadvertent mixing of anaesthetic agents in an anaesthesia machine during replenishment with new anaesthetic.

The above object is achieved in accordance with the principles of the present invention in a method and a safety system for avoiding inadvertent mixing of two different anaesthetics in an anaesthesia apparatus when a new anaesthetic from a container is added to the anaesthesia apparatus wherein a currently-employed anaesthetic is already present in gaseous and/or liquid form, wherein the identity of the new anaesthetic is determined before it comes into contact with the currently-employed anaesthetic in the anaesthesia apparatus, and wherein the new anaesthetic is allowed to come into contact with the currently-employed anaesthetic only if the new anaesthetic is the same as the currently-employed anaesthetic.

The inventive safety system and method are based on identification of new anaesthetic with a suitable measurement technique before it is allowed to come into contact with the first anaesthetic in the anaesthesia machine. Known measurement techniques include spectrophotometry, determination of the anaesthetic's refractive index, determination of the anaesthetic's density etc.

The use of a blocking unit can completely prevent new anaesthetic from coming into contact with the first anaesthetic if an error should occur. Anaesthesia can then continue without interruption at the same time as the new anaesthetic is evacuated and replenishment (possibly with intermediate cleaning of the flow channel) with correct new anaesthetic.

The measurement unit is installed at a suitable location in the anaesthesia machine on which the safety system is to be employed. In certain instances, therefore, arranging the measurement unit in the flow channel may be advantageous. In others instances, it may be advantageous, or even necessary, to arrange the measurement unit outside the flow channel, i.e. on the exterior of the anaesthesia machine.

In principle, the flow channel also can be a part of the safety system. This means, in principle, that the safety system is used as a part of a device for replenishing anaesthetic. In this instance, it would be easier to tailor a device, with a minimum of measures, to a number of different kinds of anaesthesia machines.

It is advantageous to include an alarm in the safety system to provide a warning when inadvertent mixing is about to occur.

Identifying the first anaesthetic is also advantageous for further enhancing the system's safety (without reliance on the accuracy of information entered on the identity of the first anaesthetic).

This identification can be performed by filling an empty anaesthesia machine with the first anaesthetic in the same way as the new anaesthetic. The measurement unit then can identify the first anaesthetic and send this information to a memory. When the machine is replenished with a new anaesthetic, it is easy for the system to compare the identity of the new anaesthetic with information stored about the first anaesthetic.

A second measurement unit, in contact with the first anaesthetic, can alternatively be arranged in the anaesthesia machine. Measurement and comparison of identities can then be performed simultaneously. This may be preferable in instances in which the anaesthesia machine already contains an analyzer or the like for identifying the anaesthetic in the anaesthesia machine.

DESCRIPTION OF THE PREFERRED EMBODIMENTS

Figure 1:
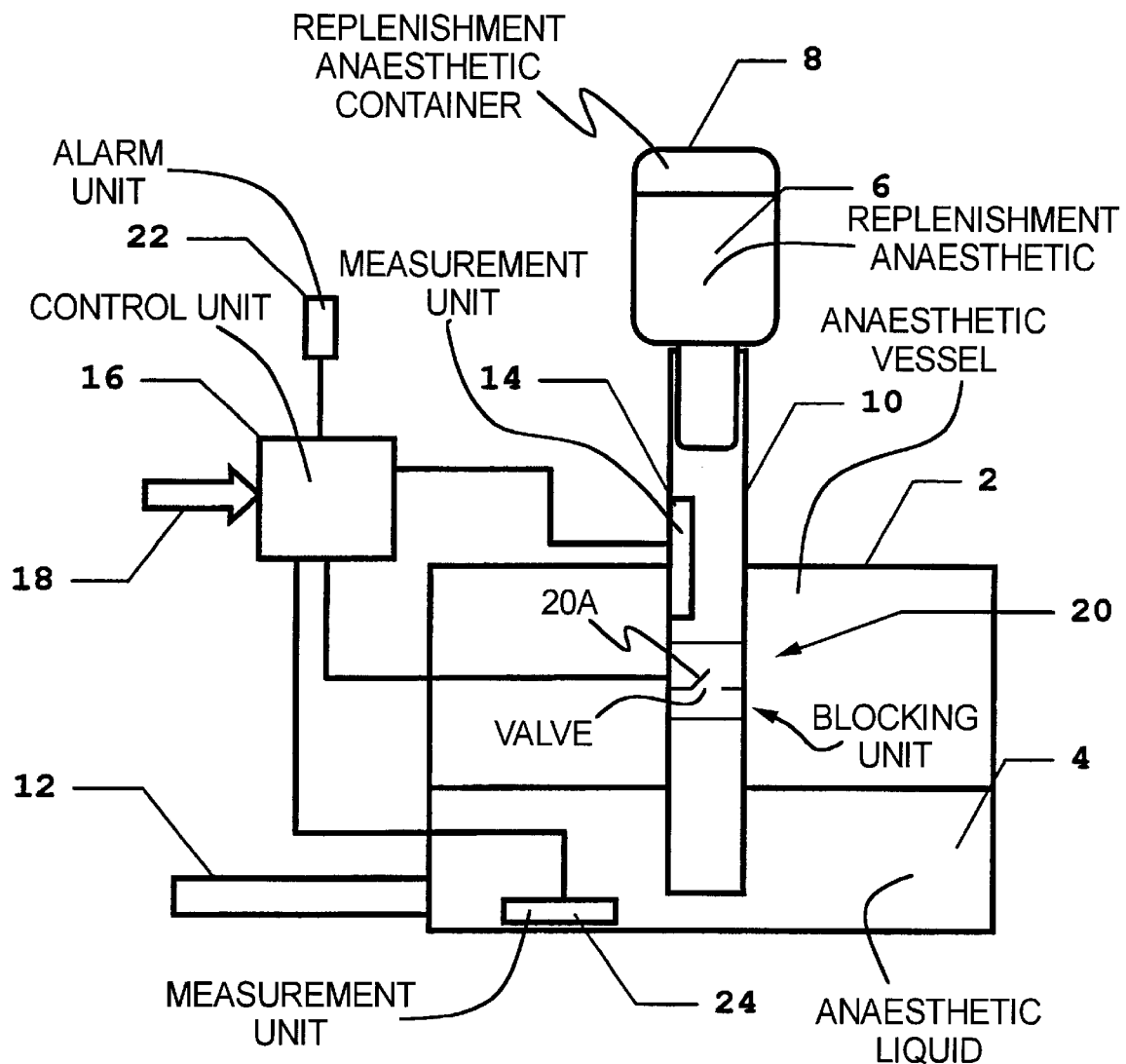
FIG. 1 shows a first embodiment of a safety system according to the invention.

FIG. 1 shows the components of an anaesthesia machine relevant to the invention. These include a vessel 2 for holding a first anaesthetic 4. The vessel 2 can be replenished with a new anaesthetic from a container 8 (a bottle in this instance) via a flow channel 10.

The first anaesthetic 4 can be dispensed or sent to a vaporizer (not shown) through a dispensing line 12.

A safety system according to the invention is connected to the anaesthesia machine to prevent inadvertent mixing of different anaesthetics when the vessel is replenished with new anaesthetic 6. FIG. 1 shows a first embodiment of this safety system.

The safety system includes a first measurement unit 14, arranged in the flow channel 10, for identifying anaesthetic in the flow channel 10, the new anaesthetic 6 in this instance. Identification information is sent to a control unit 16 that also can receive information from other sources, as indicated with an arrow 18. This additional information can e.g. be from a user interface and stipulate the anaesthetic a physician intends to use, etc.

The control unit 16 and the measurement unit 14 are depicted as separate components to clarify their respective functions. Modern computer technology makes it possible to implement all functions on a single microchip in the measurement unit 14 that then serves both as a measurement unit and control unit.

If the control unit 16 finds that the new anaesthetic 6 has the same identity as the first anaesthetic 4, a blocking unit 20 can be opened to allow the new anaesthetic 6 to pass into the vessel 2 where it mixes with the first anaesthetic 4. The blocking unit 20 can be a valve 20A, for example.

The new anaesthetic 6 then can be poured back into the container 8, and replenishment can use the correct anaesthetic (identical to the first anaesthetic) instead. It is then advantageous for the flow channel 10 first to be cleared from residual new anaesthetic 6.

The alarm unit 22 can sound an alarm at the same time as the control unit 16 determines that the new anaesthetic 6 has the wrong identity.

To ensure that the anaesthetics 4, 6 really do have the same or different identities, the safety system incorporates a second measurement unit 24, in this instance to establish the identity of the first anaesthetic 4 in the vessel 2.

In principle, this represents a virtually 100% guarantee against inadvertent mixing of anaesthetics. This also represents savings for hospitals, since surplus anaesthetic from anaesthesia can be used with great safety for the next inducement of anaesthesia. This simultaneously reduces the risk of large amounts of anaesthetic being discarded, which is the case when different anaesthetics have already mixed. Moreover, it is not necessary to interrupt or disrupt anaesthesia only because of replenishment with the wrong anaesthetic.

The first embodiment of the safety system according to the invention shows the safety system connected to an anaesthesia machine with a vessel for a first liquid anaesthetic (a conventional vaporizer on an anaesthesia machine)

Figure 2:
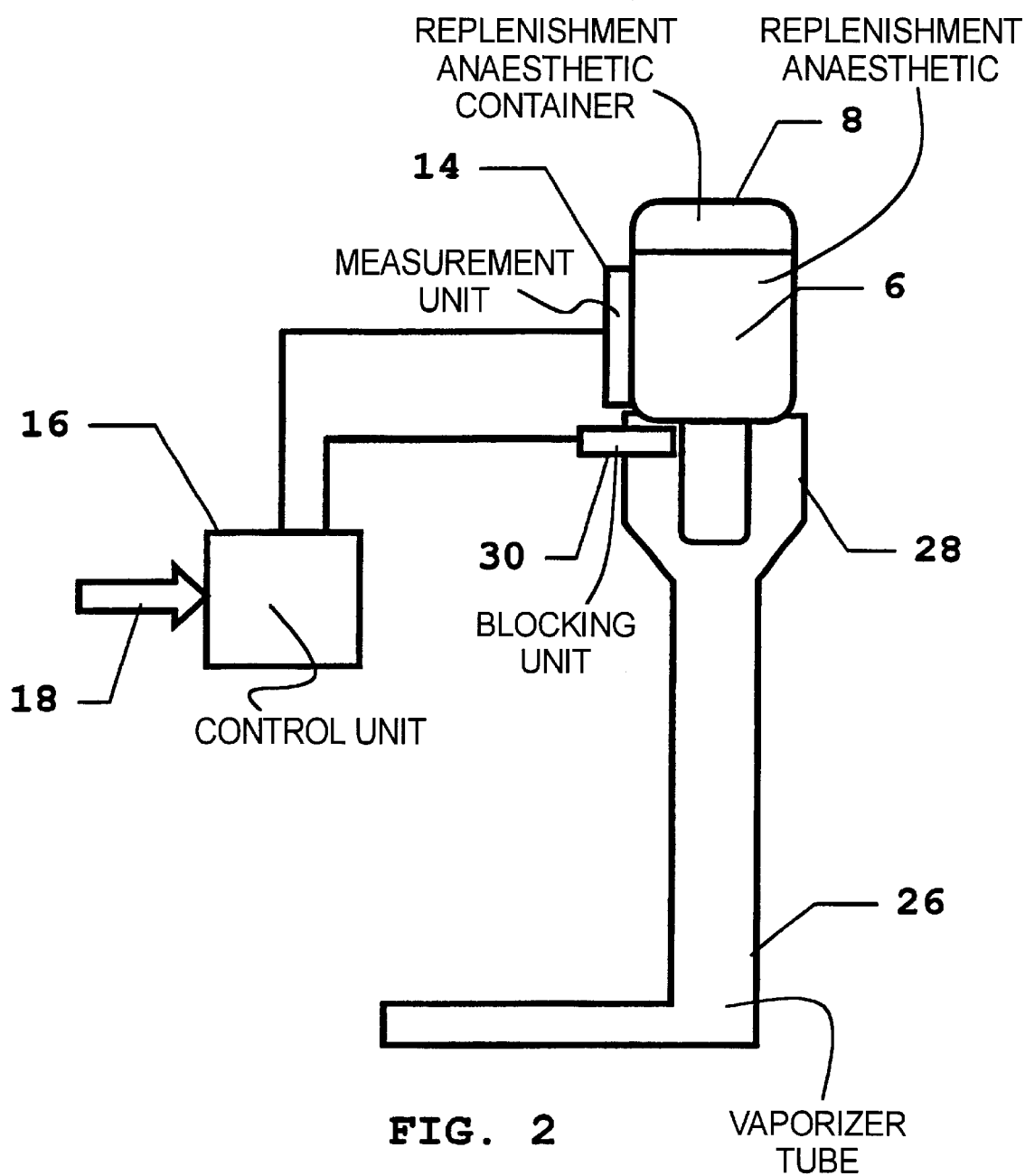
FIG. 2 shows a second embodiment of a safety system according to the invention.

In the second embodiment of the safety system according to the invention, as shown in FIG. 2, the safety system is devised for a different anaesthesia machine. Designations for identical components are the same as in FIG. 1. The anaesthesia machine in FIG. 2 utilizes the container 8 for the new anaesthetic 6, like the vessel 2 shown in FIG. 1.

A vaporizer tube 26 carries liquid anaesthetic to a vaporizing chamber (not shown) in the anaesthesia machine (some residual first anaesthetic may be present in the bifurcated tube)

A measurement unit 14 is attached to the exterior of the container 8 for identifying the new anaesthetic 6 in the container 8.

If the new anaesthetic 6 has the same identity as the first anaesthetic, the container 8 is connected to an inlet section 28 of the anaesthesia machine. The identity of the first anaesthetic can be stored in the control unit 16 in the form of programmed information, or it can be sent from a second measurement unit (not shown) in the anaesthesia machine.

When the container 8 is connected, the new anaesthetic 6 is able to flow into the vaporizer tube 26.

If the identities are not the same, a blocking unit 30 prevents the container 8 from connecting to the anaesthesia machine's inlet section 28. The blocking unit 30 can comprise one or a plurality of mechanical barriers controlled by the control unit 16.

The two embodiments show two possible versions of the safety system according to the invention. They show that the safety system is not limited to a particular type of anaesthesia machine or vaporizer system for anaesthetics. In other types of vaporizers, a carrier gas can be passed through a chamber, carrying vaporized anaesthetic with it.

An important feature of the invention (which provides a number of advantages) is identification of a new anaesthetic in anaesthetic replenishment before the new anaesthetic reaches any existing anaesthetic in the anaesthesia system.

Although modifications and changes may be suggested by those skilled in the art, it is the intention of the inventor to embody within the patent warranted hereon all changes and modifications as reasonably and properly come within the scope of his contribution to the art.

I claim as my invention:

1. A safety system for preventing inadvertent mixing of different anaesthetics in an anaesthesia apparatus having currently-employed anaesthetic liquid therein and having a flow channel communicable with a container containing a new anaesthetic for replenishing said currently-employed anaesthetic liquid, said currently-employed anaesthetic existing in said anaesthesia apparatus downstream from said flow channel, said safety system comprising:

a measurement unit adapted to interact with said new anaesthetic liquid for determining an identity of said new anaesthetic liquid, said measurement unit being disposed relative to said flow channel to determine said identity of said new anaesthetic liquid before said new anaesthetic liquid comes into contact with said currently-employed anaesthetic liquid.

2. A safety system as claimed in claim 1 wherein said measurement unit is adapted to be disposed in said flow channel.

3. A safety system as claimed in claim 1 wherein said measurement unit is disposed outside of said flow channel is adapted for connection to said container containing said new anaesthetic liquid.

4. A safety system as claimed in claim 1 further comprising a blocking unit disposed downstream from said measurement unit and enabled by a signal from said control unit to allow mixing of said new anaesthetic liquid with said currently-employed anaesthetic liquid only if said control unit determines that said new anaesthetic liquid is the same as said currently-employed anaesthetic liquid.

5. A safety system as claimed in claim 4 wherein said blocking unit comprises a valve.

6. A safety system as claimed in claim 1 further comprising an alarm unit connected to said measurement unit which emits an alarm if said measurement unit determines that said new anaesthetic liquid is different from said currently-employed anaesthetic liquid.

7. A safety system as claimed in claim 1 wherein said measurement unit is a first measurement unit, and said safety system further comprising a second measurement unit, adapted to be disposed in said anaesthesia apparatus at a location remote from said first measurement unit, said second measurement unit adapted to interact with said currently-employed anaesthetic liquid for determining an identity of said currently-employed anaesthetic liquid, and wherein said control unit is supplied with signals from said first measurement unit and said second measurement unit and compare the identity of said new anaesthetic liquid with the identity of said currently-employed anaesthetic liquid.

8. A method for avoiding inadvertent mixing of two different anaesthetics in an anaesthetic apparatus comprising the steps of:

using a currently-employed anaesthetic liquid in an anaesthesia apparatus;

replenishing said anaesthesia apparatus with a new anaesthetic liquid from a new anaesthetic container by connecting said new anaesthetic container to a flow path in the anaesthesia apparatus, said new anaesthetic liquid coming into contact with said currently-employed anaesthetic liquid downstream of said flow path;

at said anaesthetic apparatus, determining an identity of said new anaesthetic liquid before said new anaesthetic liquid comes into contact with said currently-employed anaesthetic liquid in said anaesthetic apparatus; and opening said flow path to allow said new anaesthetic liquid to come into contact with said currently-employed anaesthetic liquid in said anaesthetic apparatus only if said new anaesthetic liquid is the same as said currently-employed anaesthetic liquid.

\* \* \* \* \*